United States Patent
Ueda et al.

(10) Patent No.: US 11,013,422 B2
(45) Date of Patent: May 25, 2021

(54) BLOOD PRESSURE MEASUREMENT APPARATUS

(71) Applicant: NIHON KOHDEN CORPORATION, Tokyo (JP)

(72) Inventors: Yoshinori Ueda, Tokorozawa (JP); Kazumasa Ito, Tokorozawa (JP); Takashi Usuda, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 309 days.

(21) Appl. No.: 16/131,522

(22) Filed: Sep. 14, 2018

(65) Prior Publication Data

US 2019/0090758 A1 Mar. 28, 2019

(30) Foreign Application Priority Data

Sep. 26, 2017 (JP) .............................. JP2017-185104

(51) Int. Cl.
*A61B 5/0225* (2006.01)
*A61B 5/022* (2006.01)

(52) U.S. Cl.
CPC ........ *A61B 5/0225* (2013.01); *A61B 5/02225* (2013.01); *A61B 5/02255* (2013.01)

(58) Field of Classification Search
CPC .............. A61B 5/0225; A61B 5/02255; A61B 5/02225; A61B 5/022; A61B 5/0234
USPC ........................................ 600/485, 494, 500
See application file for complete search history.

(56) References Cited

U.S. PATENT DOCUMENTS

| | | | | |
|---|---|---|---|---|
| 5,485,838 A | * | 1/1996 | Ukawa | A61B 5/022 356/41 |
| 2003/0097074 A1 | * | 5/2003 | Oka | A61B 5/02116 600/490 |
| 2005/0119578 A1 | * | 6/2005 | Kubo | A61B 5/02116 600/490 |
| 2011/0152650 A1 | * | 6/2011 | Donehoo | A61B 5/02255 600/324 |
| 2013/0138001 A1 | * | 5/2013 | Wu | A61B 5/0235 600/493 |
| 2013/0190629 A1 | * | 7/2013 | Umeda | A61B 5/02225 600/479 |
| 2017/0172429 A1 | * | 6/2017 | Takoh | A61B 5/02225 |

FOREIGN PATENT DOCUMENTS

JP 2002-078685 A 3/2002

* cited by examiner

*Primary Examiner* — Sean P Dougherty
*Assistant Examiner* — Alexander H Connor
(74) *Attorney, Agent, or Firm* — Pearne & Gordon LLP

(57) ABSTRACT

A blood pressure measurement apparatus includes a pressure controller that controls an internal pressure of a cuff, an oscillation acquiring section that acquires an oscillation corresponding to a pressure vibration, a pulse wave signal acquiring section that acquires a pulse wave signal of the subject from a probe, a processor, and a memory that stores instructions executable by the processor. In the apparatus, when the instructions are executed by the processor, the apparatus causes the pressure controller to inflate the internal pressure, determines whether a first condition is satisfied or not, determines whether a second condition is satisfied or not, and if the first condition and the second condition are satisfied, determines a mean blood pressure of the subject based on the internal pressure.

6 Claims, 3 Drawing Sheets

BLOOD PRESSURE MEASUREMENT APPARATUS

CROSS REFERENCE TO RELATED APPLICATION

This application is based on Japanese Patent Applications No. 2017-185104 filed on Sep. 26, 2017, the contents of which are incorporated herein by reference.

BACKGROUND

The presently disclosed subject matter relates to a blood pressure measurement apparatus for noninvasively measuring the blood pressure of a subject by using a cuff.

JP-A-2002-078685 discloses a blood pressure measurement apparatus which is of a so-called pressurizing type, and which identifies the systolic blood pressure and the like of a subject while inflating the internal pressure of a cuff that is attached to the subject. A pressurizing type blood pressure measurement apparatus is differentiated from a so-called depressurizing type blood pressure measurement apparatus. A depressurizing type blood pressure measurement apparatus once raises the internal pressure of a cuff to a value which is higher than an estimated systolic blood pressure of a subject, and then identifies the systolic blood pressure and the like while deflating the internal pressure.

Usually, the measurement time period in a pressurizing type blood pressure measurement apparatus is shorter than that in a depressurizing type blood pressure measurement apparatus.

A pressurizing type blood pressure measurement apparatus explained in the disclosure improves the reliability of a result of a measurement performed.

SUMMARY

According to an aspect of the presently disclosed subject matter, a blood pressure measurement apparatus includes:
a pressure controller that controls an internal pressure of a cuff attached to a subject; an oscillation acquiring section that acquires an oscillation corresponding to a pressure vibration occurring in the cuff;
a pulse wave signal acquiring section that acquires a pulse wave signal of the subject from a probe attached to a portion of the subject that is on a distal side with respect to a portion of the subject to which the cuff is attached;
a processor; and
a memory that stores instructions executable by the processor,
wherein, when the instructions are executed by the processor, the apparatus
causes the pressure controller to inflate the internal pressure,
determines whether a first condition that an amplitude of the oscillation which is acquired by the oscillation acquiring section is switched from increasing to decreasing is satisfied or not,
determines whether a second condition that a decreasing amount of an amplitude of the pulse wave signal which is acquired by the pulse wave signal acquiring section is larger than a predetermined value is satisfied or not, and
if the first condition and the second condition are satisfied, determines a mean blood pressure of the subject based on the internal pressure.

According to another aspect of the presently disclosed subject matter, a blood pressure measurement system includes:
a cuff that is attached to a subject;
a probe that is attached to a portion of the subject which is on a distal side with respect to a portion to which the cuff is attached;
a pressure controller that controls an internal pressure of the cuff;
an oscillation acquiring section that acquires an oscillation corresponding to a pressure vibration occurring in the cuff;
a pulse wave signal acquiring section that acquires a pulse wave signal of the subject from the probe;
a processor; and
a memory that stores instructions executable by the processor,
wherein, when the instructions are executed by the processor, the system
causes the pressure controller to inflate the internal pressure,
determines whether a first condition that an amplitude of the oscillation which is acquired by the oscillation acquiring section is switched from increasing to decreasing is satisfied or not,
determines whether a second condition that a decreasing amount of an amplitude of the pulse wave signal which is acquired by the pulse wave signal acquiring section is larger than a predetermined value is satisfied or not, and
if the first condition and the second condition are satisfied, determines a mean blood pressure of the subject based on the internal pressure.

It is known that the internal pressure of a cuff at a timing when the amplitude of an oscillation has the maximum value corresponds to the mean blood pressure of a subject. When attention is focused only on the amplitude of an oscillation, however, a case may occur where the mean blood pressure cannot be correctly determined. In the above-described blood pressure measurement apparatus, in order to improve the accuracy of a result of a blood pressure measurement, the pulse wave signal of the subject which is output from the probe is used. When the internal pressure of the cuff is inflated to a value that approximately corresponds to the mean blood pressure of the subject, the amplitude of the pulse wave is decreased by the pressurization caused by the cuff in a distal portion of the subject to which the probe is attached. In view of this fact, the above-described blood pressure measurement apparatus determines the mean blood pressure in the case where the oscillation is switched from increasing to decreasing, and the decreasing amount of the amplitude of the pulse wave signal is larger than the predetermined value. Therefore, it is possible to improve the reliability of a result of a measurement of the mean blood pressure which is performed by a pressurizing type blood pressure measurement apparatus.

DETAILED DESCRIPTION OF EMBODIMENTS

Figure 1:
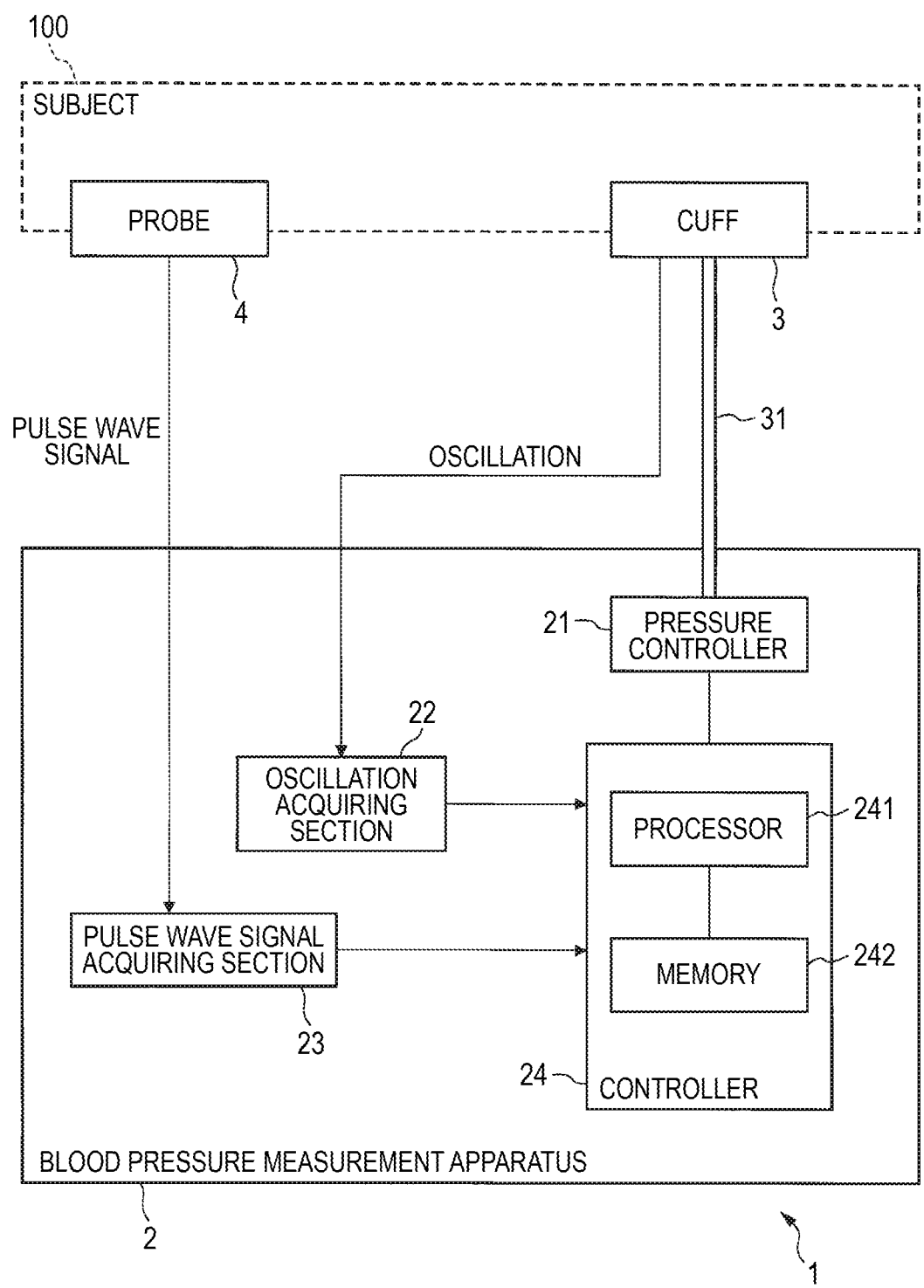
FIG. 1 illustrates the functional configuration of a blood pressure measurement system of an embodiment.

An embodiment will be described in detail with reference to the accompanying drawings. FIG. 1 illustrates the functional configuration of a blood pressure measurement system 1 of the embodiment. The blood pressure measurement system 1 includes a blood pressure measurement apparatus 2, a cuff 3, and a probe 4.

The cuff 3 and the probe 4 are to be attached to a subject 100. For example, the cuff 3 is wrapped around the upper arm of the subject 100. The probe 4 is attached to a portion of the subject 100 that is on the distal side with respect to the portion to which the cuff 3 is attached. An example of such a portion is the fingertip of the subject 100.

The probe 4 is a device which detects the pulse wave of the subject 100 by using a photoelectric sensor. Although not illustrated, the probe 4 includes a light emitter and a light detector. Examples of the light emitter are a light emitting diode (LED), a laser diode, and an organic electroluminescence (EL) element. Examples of the light detector are a photodiode, a phototransistor, and a photoresistor. A light beam emitted from the light emitter is transmitted through or reflected from the tissue of the subject 100, and then enters the light detector. The light detector outputs a signal corresponding to the intensity of the received light beam. The intensity of the received light beam is changed in accordance with a volumetric change of the blood vessel due to the pulsation, and therefore a pulse wave signal corresponding to the pulse wave of the subject 100 is obtained. The probe 4 outputs the pulse wave signal.

The blood pressure measurement apparatus 2 is an apparatus for noninvasively measuring the blood pressure of the subject 100 by using the cuff 3. The blood pressure measurement apparatus 2 includes a pressure controller 21, an oscillation acquiring section 22, a pulse wave signal acquiring section 23, and a controller 24.

The pressure controller 21 is connected to the cuff 3 through a tube 31. The pressure controller 21 includes a pump and a valve. The pump supplies the air to the cuff 3 through the tube 31, thereby inflating the internal pressure of the cuff 3. The valve forms or releases communication between the tube 31 and the ambient air. When the pump is not operated and the tube 31 communicates with the ambient air, the internal pressure of the cuff 3 is deflated.

During a period when the cuff 3 is pressurized, a pressure vibration (oscillation) occurs in the cuff 3 in accordance with the pulsation of the blood vessel of the subject 100. The oscillation is detected by a pressure sensor which is not illustrated. The pressure sensor outputs the detected oscillation. The pressure sensor may be disposed in the cuff 3, or in an air passage through which the cuff 3 and the pressure controller 21 communicate with each other.

The oscillation acquiring section 22 is an interface for acquiring the oscillation which is output from the pressure sensor. The pulse wave signal acquiring section 23 is an interface for acquiring the pulse wave signal which is output from the probe 4.

The controller 24 includes a processor 241 and a memory 242. Examples of the processor 241 are a CPU and an MPU. The memory 242 is configured so as to store instructions which are readable by the processor 241. Examples of the memory 242 are a ROM in which various instructions are stored, and a RAM having a work area in which various instructions to be executed by the processor 241 are stored.

Figure 2:
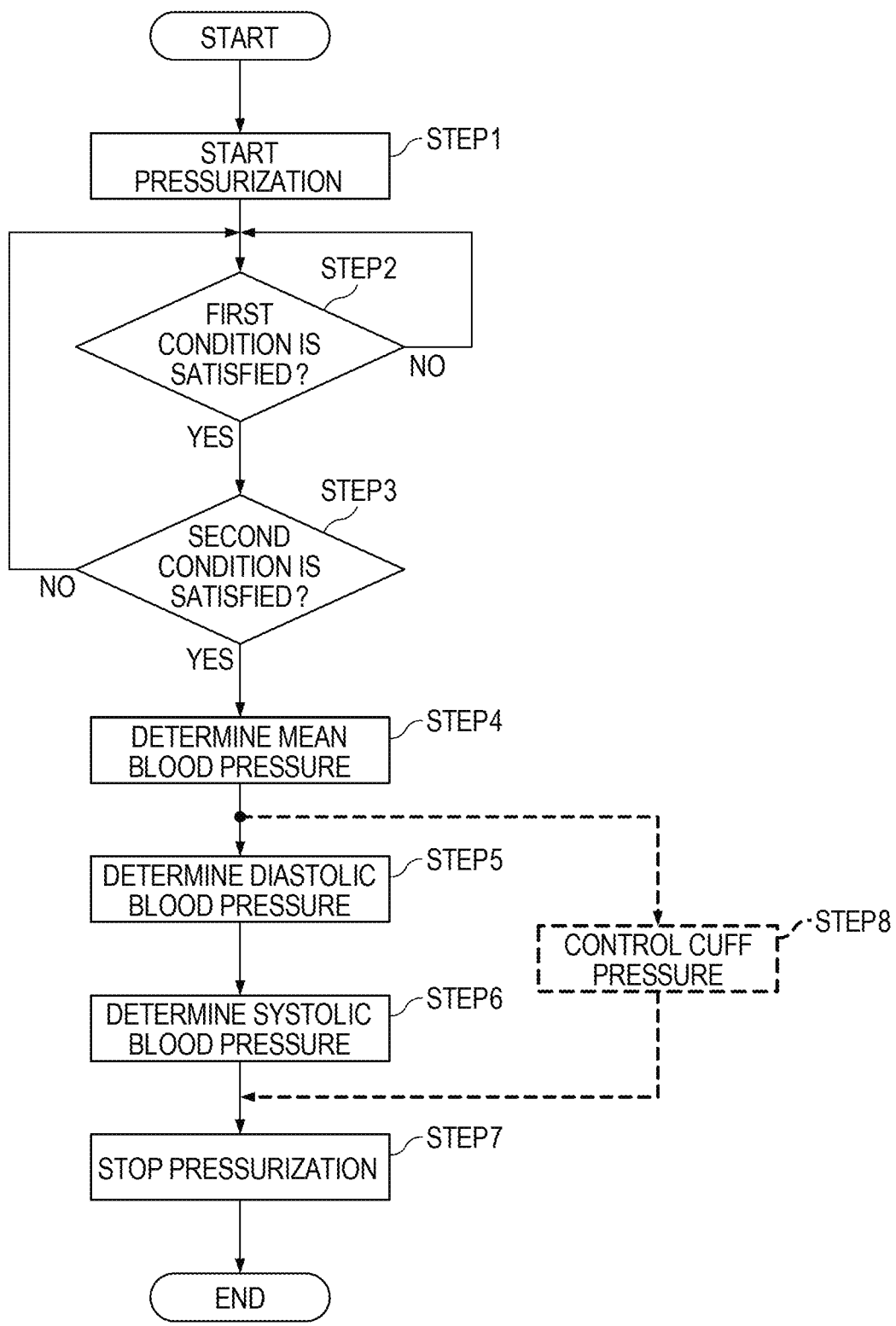
FIG. 2 is a flowchart illustrating an example of the operation of a blood pressure measurement apparatus in FIG. 1.
Figure 3:
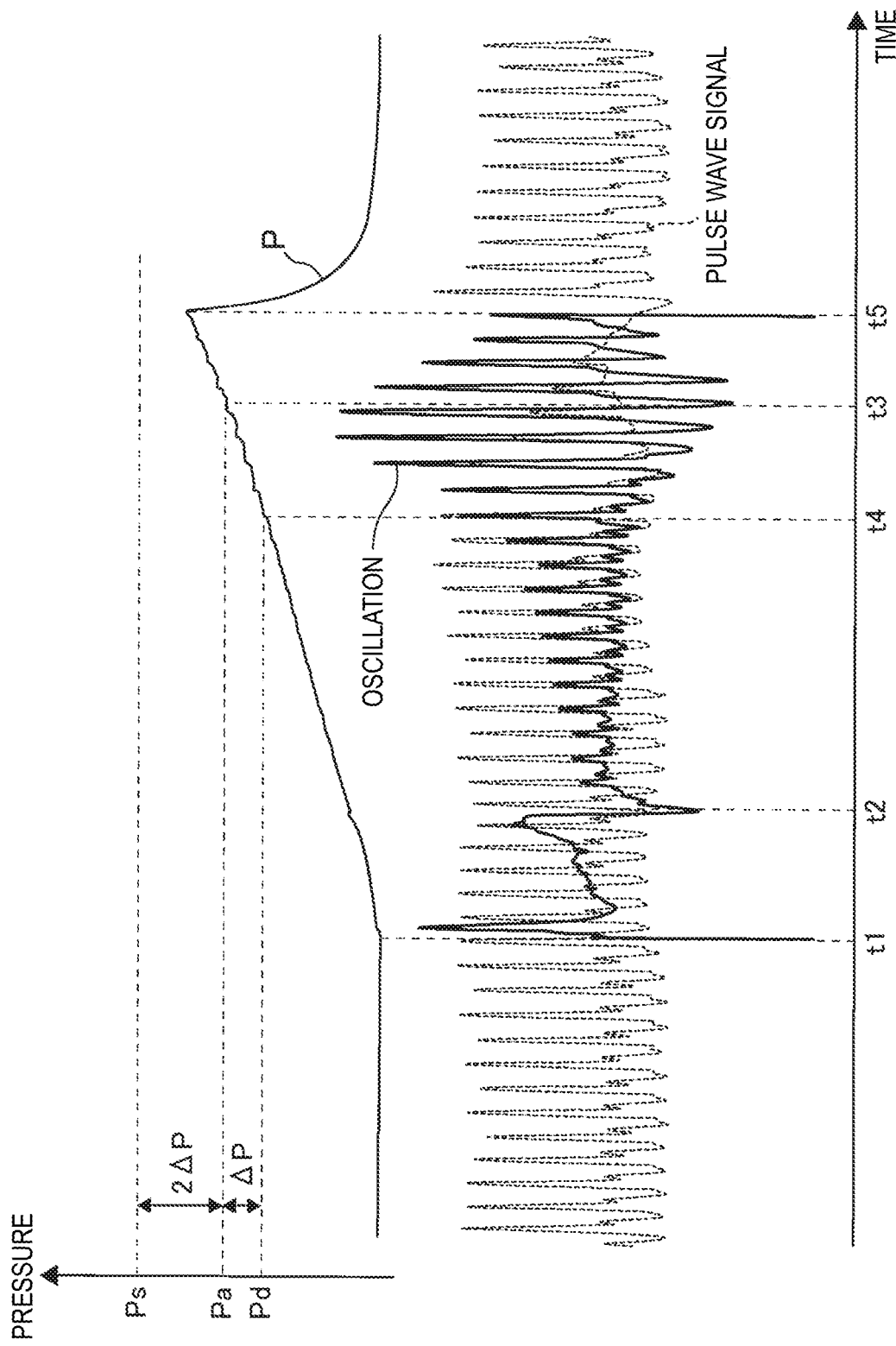
FIG. 3 illustrates an example of the operation of the blood pressure measurement apparatus in FIG. 1.

When instructions stored in the memory 242 are executed by the processor 241, the blood pressure measurement apparatus 2 executes the process illustrated in FIG. 2. FIG. 3 illustrates temporal changes of the internal pressure P in the cuff 3, the oscillation, and the pulse wave signal, based on the operation of the blood pressure measurement apparatus 2.

First, the blood pressure measurement apparatus 2 activates the pump of the pressure controller 21 to inflate the internal pressure of the cuff 3 (STEP 1). The time t1 in FIG. 3 indicates a timing of starting the pressurization of the cuff 3.

As illustrated in FIG. 3, as the internal pressure P of the cuff 3 becomes higher, the amplitude of the oscillation is gradually increased. When the internal pressure P of the cuff 3 is further inflated, the amplitude of the oscillation reaches the maximum value, and then start deflating.

The blood pressure measurement apparatus 2 determines whether a first condition that the amplitude of the oscillation which is acquired by the oscillation acquiring section 22 is switched from increasing to decreasing is satisfied or not (STEP 2). If the first condition is not satisfied (NO in STEP 2), the pressurization of the cuff 3 is continued, and the process of STEP 2 is repeated.

If the first condition is satisfied (YES in STEP 2), the blood pressure measurement apparatus 2 determines whether a second condition that the decreasing amount of the amplitude of the pulse wave signal which is acquired by the pulse wave signal acquiring section 23 is larger than a predetermined value is satisfied or not (STEP 3). The predetermined value may be the absolute value of the decreased amplitude, or the decrease rate. If the second condition is not satisfied (NO in STEP 3), the pressurization of the cuff 3 is continued, and the process is returned to STEP 2.

If both the first and second conditions are satisfied (YES in STEP 3), the blood pressure measurement apparatus 2 determines the mean blood pressure Pa of the subject 100 based on the internal pressure P of the cuff 3 (STEP 4).

The value of the internal pressure P at a timing when the amplitude of the oscillation has the maximum value corresponds to the mean blood pressure Pa of the subject 100. When attention is focused only on the amplitude of the oscillation, however, a case may occur where the mean blood pressure Pa cannot be correctly determined. At time t2 in FIG. 3, for example, the amplitude of the oscillation is once switched from increasing to decreasing. When attention is focused only on the amplitude of the oscillation, there is a possibility that it is determined that the internal pressure P of the cuff 3 at the time t2 corresponds to the mean blood pressure Pa of the subject 100.

In the embodiment, in order to improve the accuracy of a result of a blood pressure measurement, the pulse wave signal which is output from the probe 4 is used. When the internal pressure P of the cuff 3 is inflated to a value that approximately corresponds to the mean blood pressure Pa of the subject 100, the amplitude of the pulse wave is decreased by the pressurization caused by the cuff 3 in a distal portion of the subject 100 to which the probe 4 is attached. In the embodiment, in view of this fact, the mean blood pressure Pa is determined in the case where the oscillation is switched from increasing to decreasing, and the decreasing amount of the amplitude of the pulse wave signal is larger than the predetermined value.

In the waveform illustrated in FIG. 3, both the first and second conditions are satisfied at time t3. At the time t2, the first condition is satisfied, but the second condition is not satisfied, and therefore the process of STEP 4 is not performed. Consequently, the mean blood pressure Pa of the subject 100 is determined based on the internal pressure P of the cuff 3 at the time t3. As a result, it is possible to improve the reliability of a result of a measurement of the mean blood pressure Pa which is performed by the blood pressure measurement apparatus 2 that is of the pressuring type.

Next, the blood pressure measurement apparatus 2 determines the diastolic blood pressure Pd of the subject 100 (STEP 5). Specifically, a point in the past when the amplitude of the oscillation was a half of the local maximum value of the amplitude of the oscillation which is the basis for determining the mean blood pressure Pa in STEP 4 is determined. The blood pressure measurement apparatus 2 determines the diastolic blood pressure Pd of the subject 100 based on the internal pressure P of the cuff 3 at the point in time. In the case of the example illustrated in FIG. 3, at time t4, the amplitude of the oscillation has a value which is a half of the amplitude at the time t3. Therefore, the diastolic blood pressure Pd of the subject 100 is determined based on the internal pressure P of the cuff at the time t4.

Next, the blood pressure measurement apparatus 2 calculates the systolic blood pressure Ps of the subject 100 (STEP 6). As illustrated in FIG. 3, specifically, the systolic blood pressure Ps is calculated based on the following expressions.

$$Ps = Pa + 2\Delta P$$

$$\Delta P = Pa - Pd$$

The value of the determined diastolic blood pressure Pd, and that of the calculated systolic blood pressure Ps are based on the value of the mean blood pressure Pa which is verified with reference to the pulse wave signal. Therefore, it is possible to improve the reliability of results of measurements of the diastolic blood pressure Pd and the systolic blood pressure Ps which are performed by the blood pressure measurement apparatus 2 that is of the pressuring type.

Thereafter, the blood pressure measurement apparatus 2 stops the pressurization of the cuff 3 (STEP 7). Specifically, the blood pressure measurement apparatus 2 stops the pump of the pressure controller 21, and activates the valve. In the example illustrated in FIG. 3, the pressurization of the cuff 3 is stopped at time t5. As a result, the internal pressure P of the cuff 3 is deflated.

The timing when the pressurization of the cuff 3 is stopped is set to be at least after the determination of the mean blood pressure Pa of the subject 100. Namely, the stop of the pressurization of the cuff 3 may be performed in advance of the calculation of the systolic blood pressure Ps, or the determination of the diastolic blood pressure Pd. In any case, as illustrated in FIG. 3, the pressurization of the cuff 3 is stopped before the internal pressure P of the cuff 3 reaches a value corresponding to the systolic blood pressure Ps.

In the case of a pressuring type blood pressure measurement apparatus, it is not necessary to inflate the internal pressure of a cuff to a value which is higher than an estimated systolic blood pressure, and therefore the measurement time period may be shortened as compared with that in a depressurizing type blood pressure measurement apparatus. According to the configuration of the embodiment, it is not necessary to inflate the internal pressure P of the cuff 3 to a value corresponding to the systolic blood pressure Ps, and therefore the measurement time period may be further shortened. Moreover, the time period of the pressurization due to the cuff 3 may be shortened, and therefore an influence exerted on the detection of the pulse wave of the subject 100 which is performed by the probe 4 may be minimized.

The blood pressure measurement apparatus 2 further includes a displaying section which is not illustrated. The mean blood pressure Pa, diastolic blood pressure Pd, and systolic blood pressure Ps which are obtained by the above-described process may be displayed on the displaying section.

As indicated by the broken lines in FIG. 2, after the mean blood pressure Pa of the subject 100 is determined, the blood pressure measurement apparatus 2 may cause the pressure controller 21 to control the internal pressure P of the cuff 3 based on the variation of the amplitude of the pulse wave signal which is acquired by the pulse wave signal acquiring section 23 (STEP 8). Specifically, when the amplitude of the pulse wave signal becomes smaller than a predetermined value, the pressure controller 21 deflates the internal pressure P of the cuff 3, and, when the amplitude of the pulse wave signal becomes larger than the predetermined value, the pressure controller 21 inflates the internal pressure P of the cuff 3. For example, the predetermined value may be set as the value of the amplitude of the pulse wave signal which is referred in the determination of the mean blood pressure Pa.

According to the configuration, it is possible to provide a novel monitoring mode in which the mean blood pressure Pa of the subject 100 may be continuously monitored by using the noninvasive blood pressure measurement apparatus 2.

The above-described embodiment is a mere example for facilitating understanding of the presently disclosed subject matter. The configuration of the embodiment may be adequately changed or improved without departing from the spirit of the presently disclosed subject matter.

The pressure controller 21 and controller 24 of the blood pressure measurement apparatus 2 are not always required to be placed in a common housing. At least part of the function of the controller 24 may be realized by a calculating device of a computer to which the blood pressure measurement apparatus 2 is connected.

The probe 4 may be configured as a device for measuring the transcutaneous arterial oxygen saturation (SpO2) of the subject 100. In this case, the light emitter may be configured to emit a red light beam and an infrared light beam. The function of obtaining the pulse wave signal of the subject 100 is provided as one function of a probe for measuring the transcutaneous arterial oxygen saturation.

What is claimed is:

1. A blood pressure measurement apparatus comprising:
  a pressure controller that controls an internal pressure of a cuff configured to attach to a subject;
  an oscillation acquiring section including an interface that acquires an oscillation corresponding to a pressure vibration occurring in the cuff;
  a pulse wave signal acquiring section including an interface that acquires a pulse wave signal of the subject from a probe configured to attach to a portion of the subject that is on a distal side with respect to a portion of the subject to which the cuff is attached;
  a processor; and
  a memory that stores instructions executable by the processor,
  wherein, when the instructions are executed by the processor, the apparatus:
    causes the pressure controller to inflate the internal pressure, determines whether a first condition that an amplitude of the oscillation which is acquired by the oscillation acquiring section is switched from increasing to decreasing is satisfied or not, determines whether a second condition that a decreasing amount of an amplitude of the pulse wave signal which is acquired by the pulse wave signal acquiring section is larger than a predetermined value is satisfied or not, and if the first condition and the second condition are satisfied, determines a mean blood pressure of the subject based on the internal pressure.

2. The blood pressure measurement apparatus according to claim 1, wherein, when the instructions are executed by the processor, the apparatus:

determines a diastolic blood pressure of the subject, and calculates a systolic blood pressure based on the mean blood pressure and the diastolic blood pressure.

3. The blood pressure measurement apparatus according to claim 2, wherein, when the instructions are executed by the processor, the apparatus causes the pressure controller to stop inflating of the internal pressure before the internal pressure reaches a value corresponding to the systolic blood pressure.

4. The blood pressure measurement apparatus according to claim 1, wherein, when the instructions are executed by the processor, the apparatus causes the pressure controller to increase or decrease the internal pressure based on variation of the amplitude of the pulse wave signal which is acquired by the pulse wave signal acquiring section.

5. The blood pressure measurement apparatus according to claim 2, wherein, when the instructions are executed by the processor, the apparatus causes the pressure controller to increase or decrease the internal pressure based on variation of the amplitude of the pulse wave signal which is acquired by the pulse wave signal acquiring section.

6. A blood pressure measurement system comprising:

a cuff configured to attach to a subject;

a probe configured to attach to a portion of the subject which is on a peripheral side with respect to a portion to which the cuff is attached;

a pressure controller that controls an internal pressure of the cuff;

an oscillation acquiring section including an interface that acquires an oscillation corresponding to a pressure vibration occurring in the cuff;

a pulse wave signal acquiring section including an interface that acquires a pulse wave signal of the subject from the probe;

a processor; and a memory that stores instructions executable by the processor, wherein, when the instructions are executed by the processor, the system:

causes the pressure controller to inflate the internal pressure, determines whether a first condition that an amplitude of the oscillation which is acquired by the oscillation acquiring section is switched from increasing to decreasing is satisfied or not, determines whether a second condition that a decreasing amount of an amplitude of the pulse wave signal which is acquired by the pulse wave signal acquiring section is larger than a predetermined value is satisfied or not, and if the first condition and the second condition are satisfied, determines a mean blood pressure of the subject based on the internal pressure.

* * * * *